US009150547B2

(12) United States Patent
Reddy et al.

(10) Patent No.: US 9,150,547 B2
(45) Date of Patent: Oct. 6, 2015

(54) PROCESS FOR THE PREPARATION OF PAZOPANIB USING NOVEL INTERMEDIATE

(75) Inventors: Bandi Parthasaradhi Reddy, Hyderabad (IN); Kura Rathnakar Reddy, Hyderabad (IN); Dasari Muralidhara Reddy, Hyderabad (IN); Thungathurthy Srinivasa Rao, Hyderabad (IN); Bandi Vamsi Krishna, Hyderabad (IN)

(73) Assignee: HETERO RESEARCH FOUNDATION (IN)

( * ) Notice: Subject to any disclaimer, the term of this patent is extended or adjusted under 35 U.S.C. 154(b) by 0 days.

(21) Appl. No.: 13/989,541

(22) PCT Filed: Nov. 11, 2011

(86) PCT No.: PCT/IN2011/000781
§ 371 (c)(1),
(2), (4) Date: May 24, 2013

(87) PCT Pub. No.: WO2012/073254
PCT Pub. Date: Jun. 7, 2012

(65) Prior Publication Data
US 2013/0245262 A1    Sep. 19, 2013

(30) Foreign Application Priority Data
Nov. 29, 2010  (IN) .......................... 3590/CHE/2010

(51) Int. Cl.
*C07D 403/12*    (2006.01)
*C07D 239/42*    (2006.01)

(52) U.S. Cl.
CPC ............ *C07D 403/12* (2013.01); *C07D 239/42* (2013.01)

(58) Field of Classification Search
CPC ............................ C07D 403/12; C07D 239/42
See application file for complete search history.

(56) References Cited

U.S. PATENT DOCUMENTS

| 7,105,530 | B2 | 9/2006 | Boloor et al. |
| 7,262,203 | B2 | 8/2007 | Boloor et al. |
| 8,084,457 | B2 * | 12/2011 | Choidas et al. ............... 514/256 |
| 2006/0252943 | A1 | 11/2006 | Boloor et al. |
| 2008/0269170 | A1 | 10/2008 | Bosch et al. |

OTHER PUBLICATIONS

Luo et al., "Microwave-assisted synthesis of aminopyrimidines", Tetrahedron Letters, 2002, vol. 43, pp. 5739-5742, Abstract only, 2 pages.
International Search Report and Written Opinion for International Application No. PCT/IN2011/00781, International Application Filing Date: Nov. 11, 2012; Date of Mailing: May 14, 2012, 5 pages.

* cited by examiner

*Primary Examiner* — Sun Jae Yoo
(74) *Attorney, Agent, or Firm* — Cantor Colburn LLP

(57) ABSTRACT

The present invention provides a commercially viable process for preparing pazopanib and its pharmaceutically acceptable acid addition salts thereof in high yields using novel intermediate. The present invention also provides a process for the purification of pazopanib hydrochloride.

11 Claims, No Drawings

PROCESS FOR THE PREPARATION OF PAZOPANIB USING NOVEL INTERMEDIATE

CROSS-REFERENCE TO RELATED APPLICATIONS

This is a U.S. national stage of international application No. PCT/IN2011/000781, filed on 11 Nov. 2011, the disclosure of which is incorporated herein by reference in its entirety. Priority under 35 U.S.C. §119(a) and 35 U.S.C. §365(b) is claimed from IN Patent Application No. 3590/CHE/2010, filed 29 Nov. 2010, the disclosure of which is also incorporated herein by reference in its entirety.

FIELD OF THE INVENTION

The present invention provides a commercially viable process for preparing pazopanib and its pharmaceutically acceptable acid addition salts thereof in high yields using novel intermediate. The present invention also provides a process for the purification of pazopanib hydrochloride.

BACKGROUND OF THE INVENTION

U.S. Pat. No. 7,105,530 disclosed pyrimidineamines and their derivatives thereof. These compounds are antineoplastic agents, and are useful in the treatment of various cancers and renal cell carcinoma. Among them pazopanib hydrochloride, chemically 5-[4-[N-(2,3-Dimethyl-2H-indazol-6-yl)-N-methylamino]pyrimidin-2-ylamino]-2-methylbenzenesulfonamide hydrochloride. Pazopanib hydrochloride is represented by the following structure:

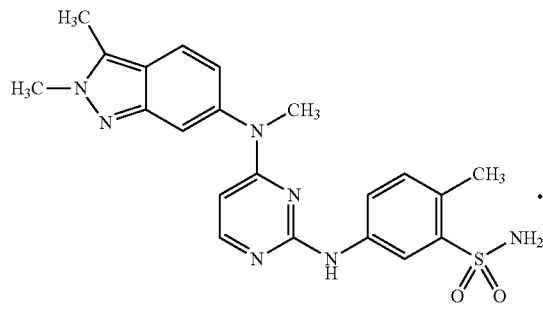

Pazopanib hydrochloride is a potent and selective multi-targeted receptor tyrosine kinase inhibitor of VEGFR (Vascular endothelial growth factor receptors)-1, VEGFR-2, VEGFR-3, PDGFR (Platelet-derived growth factor receptors)-α/β, and c-kit that blocks tumor growth and inhibits angiogenesis. It has been approved for renal cell carcinoma by the U.S. Food and Drug Administration. Pazopanib hydrochloride may also be active in ovarian cancer and soft tissue sarcoma. Pazopanib hydrochloride also appears effective in the treatment of non-small cell lung carcinoma. Pazopanib hydrochloride is marketed under the brand name Votrient® by Glaxosmithkline in the form of tablet.

Processes for the preparation of pazopanib hydrochloride and related compounds were disclosed in U.S. Pat. No. 7,105,530 and U.S. Pat. No. 7,262,203.

According to U.S. Pat. No. 7,105,530, pazopanib hydrochloride can be prepared by reacting the N-(2-chloropyrimidin-4-yl)-N,2,3-trimethyl-2H-indazol-6-amine with 5-amino-2-methylbenzenesulfonamide in the presence of hydrochloric acid in isopropanol and ether.

U.S. patent application publication no. 2006/0252943 disclosed a process for the preparation of pazopanib hydrochloride. According to this patent, pazopanib hydrochloride can be prepared by reacting the N-(2-chloropyrimidin-4-yl)-N,2,3-trimethyl-2H-indazol-6-amine with 5-amino-2-methylbenzenesulfonamide in the presence of hydrochloric acid in ethanol or methanol or tetrahydrofuran or acetonitrile and dioxane.

We have discovered a novel process for the preparation of pazopanib using novel intermediate. The process of the invention results in higher yields compared with the known process.

We have also discovered a process for the purification of pazopanib hydrochloride.

Thus, one object of the present invention is to provide a novel process for preparing pazopanib and pharmaceutically acceptable acid addition salts of pazopanib in high yields using novel intermediate.

Another object of the present invention is to provide a process for the purification of pazopanib hydrochloride.

DETAILED DESCRIPTION OF THE INVENTION

As used herein the term "room temperature" refers to a temperature of about 25° C. to about 35° C.

According to one aspect of the present invention, there is provided a novel process for the preparation of pazopanib of formula I:

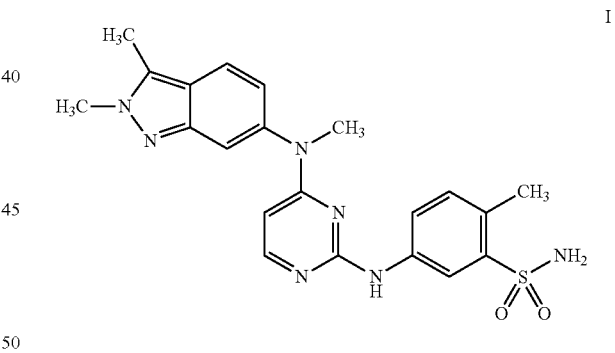

or a pharmaceutically acceptable salt thereof:
which comprises:
a) reacting 5-amino-2-methylbenzenesulfonamide of formula II:

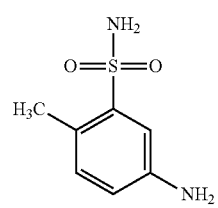

with a 2,4-dichloropryrimidine of formula III:

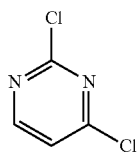

in the presence of a base and a solvent to give 5-(4-chloropyrimidin-2ylamino)-2-methylbenzenesulfonamide of formula IV; and

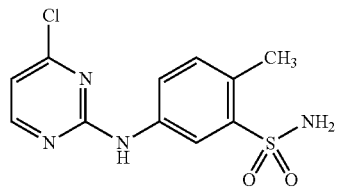

b) condensing the 5-(4-chloropyrimidin-2ylamino)-2-methylbenzenesulfonamide of formula IV with the N,2,3-trimethyl-2H-indazol-6-amine of formula V:

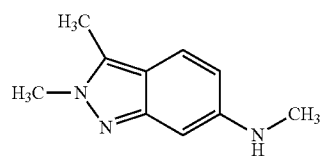

in an alcoholic solvent to give a pazopanib of formula I and optionally converting pazopanib formed into the pharmaceutically acceptable acid addition salt of pazopanib.

The base used in step (a) may preferably be an organic base or inorganic base and more preferably the base is inorganic base selected from alkali metal hydroxides, alkali metal carbonates or alkali metal bicarbonates. Still more preferably the inorganic base is sodium bicarbonate or potassium bicarbonate.

Preferably the solvent used in step (a) may be a solvent or mixture of solvents selected from methanol, ethanol, isopropyl alcohol, n-butanol, toluene, xylene, n-hexane, cyclohexane, methylene chloride, ethylene dichloride, chloroform, carbon tetrachloride, acetone, diethyl ketone, methyl ethyl ketone, methyl propyl ketone, methyl isobutyl ketone, methyl tert-butyl ketone, ethyl acetate, methyl acetate, isopropyl acetate, tert-butyl acetate, ethyl formate, methyl formate, tetrahydrofuran, diethyl ether, diisopropyl ether, tert-butyl methyl ether, dimethylformamide, N,N-dimethyl acetamide and dimethyl sulfoxide. Most preferably the solvents are methanol, ethanol, tetrahydrofuran and diisopropyl ether, and still more preferably the solvents are ethanol and tetrahydrofuran.

The reaction in step (a) may preferably be carried out at ambient temperatures in the range from about −25° C. to 100° C., more preferably at about 0° C. to 90° C. and still more preferably at about 0° C. to 80° C.

The alcoholic solvent used in step (b) may preferably be a solvent or mixture of solvents selected from methanol, ethanol, isopropyl alcohol and n-butanol, and more preferably the alcoholic solvent is ethanol or methanol.

The reaction in step (b) may preferably be carried out at an elevated temperature. The term "elevated temperature" refers to temperature at above 25° C. More preferably the step (b) is carried out at reflux.

According to another aspect of the present invention, there is provided a novel compound of formula IV:

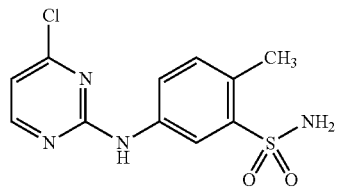

According to another aspect of the present invention, there is provided a pazopanib or a salt thereof having a purity of at least 99.9%.

According to another aspect of the present invention, there is provided a process for the purification of pazopanib hydrochloride, which comprises crystallizing pazopanib hydrochloride from a solvent system comprising alcohol solvent and water and isolating substantially pure pazopanib hydrochloride.

The term "substantially pure pazopanib hydrochloride" refers to pazopanib hydrochloride having the purity greater than about 98% by weight, preferably greater than about 99% by weight, and more preferably greater than about 99.9% by weight.

The alcoholic solvent used in the process may preferably be a solvent or mixture of solvents selected from methanol, ethanol, isopropanol and n-butanol, and more preferably the alcoholic solvent is methanol or isopropanol. Still more preferably the alcoholic solvent is methanol.

Isolation of substantially pure pazopanib hydrochloride in the process can be performed by conventional methods such as cooling, removal of solvents, concentrating the reaction mass, adding an anti-solvent, extraction with a solvent and the like.

The purity of pazopanib hydrochloride is measured by High performance liquid chromatography (HPLC).

The invention will now be further described by the following example, which is illustrative rather than limiting.

EXAMPLES

Example 1

Preparation of 5-(4-chloropyrimidin-2ylamino)-2-methylbenzenesulfonamide

To a mixture of 5-amino-2-methylbenzenesulfonamide (20 gm) in ethanol (208 ml) and tetrahydrofuran (52 ml) was added 2,4-dichloropryrimidine (44 gm) and sodium bicarbonate (36 gm) at room temperature. The contents were heated to 70 to 75° C. and maintained for 13 hours. The reaction mass was then cooled to 10° C. and maintained for 2 hours. The reaction mass was filtered and the solvent was distilled off under vacuum at below 50 to 55° C. to obtain a residual mass. To the residual mass was added ethyl acetate (100 ml) and stirred for 1 hour, filtered. The solid obtained was dried to give 15.5 gm of 5-(4-chloropyrimidin-2ylamino)-2-methylbenzenesulfonamide.

Example 2

Preparation of N,2,3-trimethyl-2H-indazol-6-amine

Sodium methoxide (19 gm) was dissolved in methanol (610 ml) and then added 2,3-dimethyl-2H-indazol-6-amine (13 gm). The reaction mixture was stirred for 15 minutes and then added paraformaldehyde (3.9 gm). The contents were heated to 60° C. and stirred for 10 hours. The reaction mass was then cooled to room temperature and maintained for 4 hours 30 minutes. Sodium borohydride (2.8 gm) was added to the reaction mass slowly at room temperature and then heated to reflux. The reaction mass was maintained for 2 hours at reflux and then cooled to room temperature. The reaction mass was stirred for 14 hours at room temperature and then added sodium hydroxide solution (1M, 100 ml). The pH of the reaction mass was adjusted to 8.0 to 8.5 with hydrochloric acid solution (40 ml) and then added ethyl acetate (400 ml). Then the layers were separated and the aqueous layer was extracted with ethyl acetate. The organic layer was dried with sodium sulfate and treated with carbon. The combined organic layers were washed with sodium chloride solution and dried with sodium sulfate. The organic layer was treated with carbon and filtered through hi-flow bed. The solvent was distilled off under vacuum at below 50° C. to obtain a residual mass. To the residual mass was added diisopropyl ether (75 ml) and stirred for 1 hour, filtered. The solid obtained was dried to give 10 gm of N,2,3-trimethyl-2H-indazol-6-amine.

Example 3

Preparation of Pazopanib Hydrochloride 5-(4-Chloropyrimidin-2ylamino)-2-methylbenzene-sulfonamide (17 gm) as obtained in example 1, N,2,3-trimethyl-2H-indazol-6-amine (10 gm) as obtained in example 2 and ethanol (166 ml) were added at room temperature and then heated to reflux. The reaction mass was maintained for 3 hours at reflux and then added concentrated hydrochloric acid (1 ml). The reaction mass was maintained for 10 hours at reflux and then cooled to room temperature. The separated solid was filtered and dried to obtain 17 gm of pazopanib hydrochloride (HPLC Purity: 97.5%).

Example 4

Purification of Pazopanib Hydrochloride

Pazopanib hydrochloride (5 gm; HPLC Purity: 97.5%) as obtained in example 3 was dissolved in a mixture of methanol (100 ml) and water (10 ml) at room temperature and then heated to reflux. The reaction mass was maintained for 30 minutes at reflux and filtered. The filtrate obtained was cooled to room temperature and maintained for 2 hours at room temperature. The solid obtained was collected by filtration and dried to obtain 3.5 gm of pazopanib hydrochloride (HPLC Purity: 99.9%).

Example 5

Purification of Pazopanib Hydrochloride

Pazopanib hydrochloride (22 gm; HPLC Purity: 98%), methanol (528 ml), water (55 ml) and concentrated hydrochloric acid (0.2 ml) were added at room temperature. The contents were heated to reflux and maintained for 30 minutes, filtered. Take the filtrate and the solvent was distilled off under vacuum to obtain a residual mass. The residual mass was then cooled to room temperature and stirred for 30 minutes at room temperature. The contents were further cooled to 0 to 5° C., stirred for 1 hour and filtered. The solid obtained was dried to give 19 gm of pazopanib hydrochloride (HPLC Purity: 99.85%).

Example 6

Purification of Pazopanib Hydrochloride

Pazopanib hydrochloride (10 gm; HPLC Purity: 96%), methanol (250 ml), water (25 ml) and concentrated hydrochloric acid (0.1 ml) were added at room temperature. The contents were heated to reflux and maintained for 30 minutes, filtered. The filtrate obtained was then cooled to room temperature and stirred for 30 minutes at room temperature. The contents further cooled to 0 to 10° C. and stirred for 1 hour. The separated solid was filtered and dried to obtain 6.6 gm of pazopanib hydrochloride (HPLC Purity: 99.8%).

Example 7

Purification of Pazopanib Hydrochloride

Pazopanib hydrochloride (22 gm; HPLC Purity: 97%) was dissolved in a mixture of isopropanol (132 ml) and water (20 ml) at room temperature and then heated to reflux. The reaction mass was maintained for 1 hour at reflux and then cooled to room temperature. The reaction mass was stirred for 1 hour at room temperature and filtered. The solid obtained was dried to give 18 gm of pazopanib hydrochloride (HPLC Purity: 99.8%).

We claim:
1. A novel process for the preparation of pazopanib of formula I:

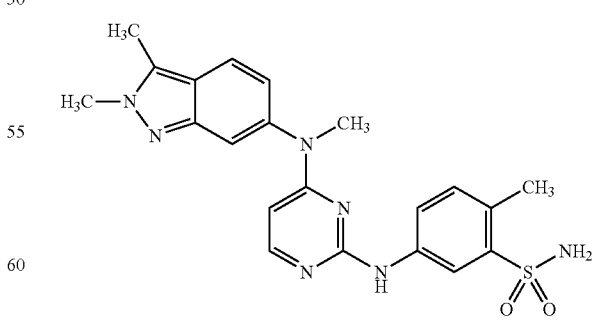

or a pharmaceutically acceptable salt thereof:
which comprises:
a) reacting 5-amino-2-methylbenzenesulfonamide of formula II:

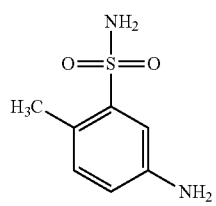

with a 2,4-dichloropryrimidine of formula III:

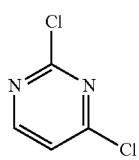

in presence of a base and a solvent to give 5-(4-chloropyrimidin-2ylamino)-2-methylbenzenesulfonamide of formula IV; and

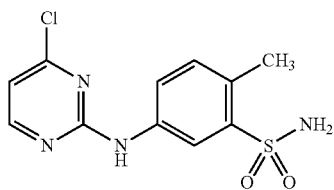

b) condensing the 5-(4-chloropyrimidin-2ylamino)-2-methylbenzenesulfonamide of formula IV with the N,2,3-trimethyl-2H-indazol-6-amine of formula V:

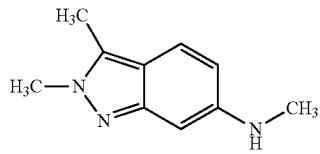

in an alcoholic solvent to give a pazopanib of formula I and optionally converting pazopanib formed into the pharmaceutically acceptable acid addition salt of pazopanib.

2. The process as claimed in claim 1, wherein the base used in step (a) is an organic base or inorganic base.

3. The process as claimed in claim 2, wherein the base is inorganic base selected from alkali metal hydroxides, alkali metal carbonates or alkali metal bicarbonates.

4. The process as claimed in claim 3, wherein the inorganic base is sodium bicarbonate or potassium bicarbonate.

5. The process as claimed in claim 1, wherein the solvent is a solvent or mixture of solvents selected from methanol, ethanol, isopropyl alcohol, n-butanol, toluene, xylene, n-hexane, cyclohexane, methylene chloride, ethylene dichloride, chloroform, carbon tetrachloride, acetone, diethyl ketone, methyl ethyl ketone, methyl propyl ketone, methyl isobutyl ketone, methyl tert-butyl ketone, ethyl acetate, methyl acetate, isopropyl acetate, tert-butyl acetate, ethyl formate, methyl formate, tetrahydrofuran, diethyl ether, diisopropyl ether, tert-butyl methyl ether, dimethylformamide, N,N-dimethyl acetamide and dimethyl sulfoxide.

6. The process as claimed in claim 5, wherein the solvents are methanol, ethanol, tetrahydrofuran and diisopropyl ether.

7. The process as claimed in claim 1, wherein the alcoholic solvent used in step (b) is a solvent or mixture of solvents selected from methanol, ethanol, isopropyl alcohol and n-butanol.

8. The process as claimed in claim 7, wherein the alcoholic solvent is ethanol or methanol.

9. The process as claimed in claim 1, wherein the reaction in step (b) is carried out at an elevated temperature.

10. The process as claimed in claim 9, wherein the reaction in step (b) is carried out at above 25° C.

11. A novel compound of formula IV:

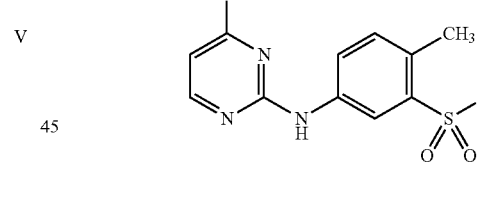

* * * * *